(12) United States Patent
Evdokimov et al.

(10) Patent No.: US 8,050,873 B2
(45) Date of Patent: Nov. 1, 2011

(54) CRYSTAL OF HYPOXIA INDUCIBLE FACTOR 1 ALPHA PROLYL HYDROXYLASE

(75) Inventors: Artem Gennady Evdokimov, Loveland, OH (US); Richard Masaru Kawamoto, Lebanon, OH (US); Angelique Sun Boyer, West Chester, OH (US); Marlene Jan Mekel, Ross, OH (US); Matthew Eugene Pokross, Hamilton, OH (US); Richard Lee Walter, Jr., Hamilton, OH (US)

(73) Assignee: Warner Chilcott Company, Fajardo, PR (US)

( * ) Notice: Subject to any disclaimer, the term of this patent is extended or adjusted under 35 U.S.C. 154(b) by 0 days.

(21) Appl. No.: 12/473,536

(22) Filed: May 28, 2009

(65) Prior Publication Data
US 2009/0240475 A1   Sep. 24, 2009

Related U.S. Application Data

(62) Division of application No. 11/713,941, filed on Mar. 5, 2007, now Pat. No. 7,588,924.

(60) Provisional application No. 60/779,898, filed on Mar. 7, 2006.

(51) Int. Cl.
*G01N 31/00* (2006.01)
*G01N 33/567* (2006.01)
*G06G 7/58* (2006.01)
*C12Q 1/26* (2006.01)

(52) U.S. Cl. ............. 702/27; 703/11; 435/25; 435/7.21
(58) Field of Classification Search .................. None
See application file for complete search history.

(56) References Cited

U.S. PATENT DOCUMENTS

| | | | |
|---|---|---|---|
| 5,620,995 A | 4/1997 | Weidmann et al. | |
| 6,020,350 A | 2/2000 | Weidmann et al. | |
| 6,566,088 B1 | 5/2003 | McKnight et al. | |
| 6,589,758 B1 | 7/2003 | Zhu | |
| 7,183,287 B2 | 2/2007 | Durley | |
| 2002/0192737 A1 | 12/2002 | Kaelin, Jr. et al. | |
| 2003/0153503 A1 | 8/2003 | Klaus et al. | |
| 2003/0176317 A1 | 9/2003 | Guenzler-Pukall et al. | |
| 2004/0254215 A1 | 12/2004 | Arend et al. | |
| 2005/0143402 A1* | 6/2005 | Cheetham et al. | 514/266.21 |
| 2006/0276477 A1 | 12/2006 | Klaus et al. | |
| 2007/0020684 A1* | 1/2007 | Bledsoe et al. | 435/7.1 |
| 2007/0154482 A1 | 7/2007 | Sukhatme et al. | |
| 2007/0213335 A1 | 9/2007 | Fitch et al. | |
| 2007/0299086 A1 | 12/2007 | Kawamoto et al. | |
| 2008/0124740 A1 | 5/2008 | Evdokimov et al. | |
| 2008/0213404 A1 | 9/2008 | Johnson et al. | |
| 2009/0082357 A1 | 3/2009 | Fitch et al. | |

FOREIGN PATENT DOCUMENTS

| | | |
|---|---|---|
| WO | WO 97/41103 | 11/1997 |
| WO | WO 02/074980 A2 | 9/2002 |
| WO | WO 02/074981 A2 | 9/2002 |
| WO | WO 03/028663 A2 | 4/2003 |
| WO | WO 2004/035812 A2 | 4/2004 |
| WO | WO 2005/118836 A2 | 12/2005 |
| WO | WO 2006/114213 A1 | 11/2006 |
| WO | WO 2007/038571 A2 | 4/2007 |
| WO | WO 2007/047194 A2 | 4/2007 |
| WO | WO 2007/070359 A2 | 6/2007 |
| WO | WO 2007/082899 A1 | 7/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/089051 A1 | 7/2008 |
| WO | WO 2008/089052 A2 | 7/2008 |
| WO | WO 2008/130508 A1 | 10/2008 |
| WO | WO 2008/130527 A1 | 10/2008 |
| WO | WO 2008/137060 A1 | 11/2008 |
| WO | WO 2008/144266 A1 | 11/2008 |
| WO | WO 2009/019656 A1 | 2/2009 |
| WO | WO 2009/037570 A2 | 3/2009 |
| WO | WO 2009/039321 A1 | 3/2009 |
| WO | WO 2009/039323 A1 | 3/2009 |
| WO | WO 2009/043093 A1 | 4/2009 |
| WO | WO 2009/049112 A1 | 4/2009 |
| WO | WO 2009/067790 A1 | 6/2009 |
| WO | WO 2009/070644 A1 | 6/2009 |
| WO | WO 2009/073497 A2 | 6/2009 |
| WO | WO 2009/073669 A1 | 6/2009 |
| WO | WO 2009/086044 A1 | 7/2009 |
| WO | WO 2009/086592 A1 | 7/2009 |
| WO | WO 2009/089547 A1 | 7/2009 |

OTHER PUBLICATIONS

Flower, "Drug Design, Cutting Edge Approaches," Royal Society of Chemistry, Cambridge, UK, 2002.*
Brucz, K., "HIF Prolyl 4-Hydroxylase (PHD) Activity and Structure Analysis: Blueprints For Development of Specific Substrate Inhibitors", Dissertation, University of New York at Buffalo, 2005.*
Bartlett et al., "Molecular Recognition in Chemical and Biological Problems,"*Special Pub., Royal Chem. Soc.*, 78, 182-196 Caveat: A Program to Facilitate the Structure-derived Design of Biologically Active Molecules (Apr. 1989). Böhm, "The Computer Program LUDI: A New Method for the Novo Design of Enzyme Inhibitors," *J. Computer-Aided Molecular Design*,6:61-78 (1992).
Bussolino, "Molecular Mechanisms of Blood Vessel Formation," *Trends Biochem. Sci.*,22(7):251-256 (1997).
Cunliffe et al., "Novel Inhibitors of Prolyl 4-Hydroxylase 3 Inhibition by the Substrate Analogue N-Oxaloglycine and Its Derivatives," *J. Med. Chem.*35:2652-2658 (1992).
Elson et al., "Induction of Hypervascularity Without Leakage or Inflammation in Transgenic Mice Overexpressing Hypoxia-Indicible Factor-1α," *Genes & Dev.*, 15:2520-2532 (2001).
Flower, "Modelling G-protein-coupled receptors for drug design," *Biochimica et Biophysica Acta*, 1422:207-234 (1999).
Folkman et al., "Tumor Angiogenesis," *The Molecular Basis of Cancer*, Mendelsohn et al., eds., W. B. Saunders, Chapter 10, pp. 206-232 (1995).
Franklin et al., "Approaches to the Design of Anti-Fibrotic Drugs," *Biochem Soc Trans.*, 19(4):812-5 (Nov. 1991).

(Continued)

*Primary Examiner* — David J Steadman
(74) *Attorney, Agent, or Firm* — Richard S. Echler

(57) ABSTRACT

The crystal structure of ligand-bound EGLN1 catalytic domain of prolyl hydroxylase is disclosed. These coordinates are useful in computer aided drug design for identifying compounds that regulate EGLN1 prolyl hydroxylase and thereby regulate HIF-regulated disorders.

15 Claims, 4 Drawing Sheets

OTHER PUBLICATIONS

Goodford, "A Computational Procedure for Determining Energetically Favorable Binding Sites on Biologically Important Macromolecules," *J. Med. Chem.*, 28(7):849-857 (1985).

Goodsell et al., "Automated Docking of Substrates to Proteins by Simulated Annealing," *Proteins: Structure, Function, and Genetics*, 8:195-202 (1990).

Jones et al., "Molecular Recognition of Receptor Sites Using a Genetic Algorithm with a Description of Desolvation," *J. Mol. Biol.*, 245:43-53 (1995).

Kaelin, "Proline Hydroxylation and Gene Expression," *Annu. Rev. Biochem.*, 74:115-125 (2005).

Krantz, "Erythropoietin," *Blood*, 77:419-434 (1991).

Kuntz et al., "A Geometric Approach to Macromolecule—Ligand Interactions," *J. Mol. Biol.*, 161:269-288 (1982).

Lee et al., "Structure of Human FIH-1 Reveals a Unique Active Site Pocket and Interaction Sites for HIF-1 and von Hippel Lindau," *JBC*, 278:7558-7563 (2003).

Li et al., "PR39, A Peptide Regulator of Angiogenesis," *Nat Med.*, 6(1):49-55 (2000).

Mancini et al., "Effect of Erythropoietin on Exercise Capacity in Patients with Moderate to Severe Chronic Heart Failure," *Circulation*, 107:294-299 (2003).

McDonough et al., "Cellular Oxygen Sensing: Crystal Structure of Hypoxia-Inducible Factor Prolyl Hydroxylase (PHD2)," *PNAS*, 103(26):9814-9819 (2006).

Miranker et al., "Functionality Maps of Binding Sites: A Multiple Copy Simultaneous Search Method," *Proteins: Structure, Function and Genetics*, 11:29-34 (1991).

Nguyen et al., "Cellular Interactions in Vascular Growth and Differentiation," *Int. Review of Cytology*, 204:1-48 (2001).

Nishibata et al., "Automatic Creation of Drug Candidate Structures Based on Receptor Structure. Starting Point for Artificial Lead Generation," *Tetrahedron*, 47(43):8985-8990 (1991).

O'Reilly et al., "Angiostatin: A Novel Angiogenesis Inhibitor that Mediates the Suppression of Metastases by a Lewis Lung Carcinoma," *Cell*, 79:315-328 (1994).

O'Reilly et al., "Endostatin: An Endogenous Inhibitor of Angiogenesis and Tumor Growth," *Cell*, 88:277-285 (1997).

Peyssonnaux et al.,"HIF-1α Expression Regulates the Bactericidal Capacity of Phagocytes," *J. Clinical Invest.*, 115(7):1806-1815 (Jul. 2005).

Schoneberg et al., "Structural Basis of G Protein-Coupled Receptor Function," *Molecular and Cellular Endocrinology*, 151:181-193 (1999).

Semenza et al., "Transcriptional Regulation of Genes Encoding Glycolytic Enzymes by Hypoxia-Inducible Factor 1," *J. Biol. Chem.*, 269:23757-23763 (1994).

Semenza, "Regulation of Erythropoietin Production: New Insights into Molecular Mechanisms of Oxygen Homeostasis," *Hematol. Oncol. Clin. North Am.*, 8:863-884 (1994).

Semenza, "Signal Transduction to Hypoxia-inducible Factor 1," *Biocehm Pharmacol*, 64:993-998 (2002).

Sexton, "Recent advances in our understanding of peptide hormone receptors and RAMPS," *Current Opinion in Drug Discovery and Development*, 2(5):440-448 (1999).

Sheehan, "3-Hydroxypicolinic Acid and Some of its Derivatives," *J. Organic Chemistry* 31(3):636-638 (1996).

Teicher et al., "Potentiation of Cytotoxic Cancer Therapies by TNP-470 Alone and with Other Anti-Angiogenic Agents," *Int. J. Cancer*, 57:920-925 (1994).

Vincent et al., "Angiogenesis is Induced in a Rabbit Model of Hindlimb Ischemia by Naked DNA Encoding an HIF-1α/VP16 Hybrid Transcription Factor," *Circulation*, 102:2255-2261 (2000).

Warnecke et al., "Activation of the Hypoxia-Inducible Factor Pathway and Stimulation of Angiogenesis by Application of Prolyl Hydroxylase Inhibitors," *FASEB Journal*, 17:1186-1188 (2003).

Wax et al., "SM-20 is a Novel 20-kd Protein Whose Expression in the Arterial Wall is Restricted to Smooth Muscle," *Lab. Invest.*, 74(4):797-808 (1996).

Weidner et al., "Tumor Angiogenesis and Metastasis—Correlation in Invasive Breast Carcinoma," *New Eng. J. Med.*, 324(1):1-8 (1991).

Wright et al., "Activation of the Prolyl Hydroxylase Oxygen-Sensor Results in Induction of GLUT1, Heme Oxygenase-1, and Nitric-Oxide Synthase Proteins and Confers Protection from Metabolic Inhibition to Cardiomyocytes," *J. Bio. Chem.*, 278(22):20235-20239 (2003).

U.S. Appl. No. 11/821,936, filed Jun. 26, 2007, Kawamoto.

* cited by examiner

Figure 5A                    Figure 5B

CRYSTAL OF HYPOXIA INDUCIBLE FACTOR 1 ALPHA PROLYL HYDROXYLASE

CROSS REFERENCE TO RELATED APPLICATIONS

This application is a Divisional Application of U.S. patent application Ser. No. 11/713,941, filed Mar. 5, 2007, now U.S. Pat. No. 7,588,924, which claims the benefit of U.S. Provisional Application No. 60/779,898 filed Mar. 7, 2006, both of which are incorporated herein by reference in their entirety.

REFERENCE TO ELECTRONIC SUBMISSION OF A TABLE

This Application contains a data table (designated as Table 2 in the specification) as an appendix via EFS-Web Filing as required under 37 CFR §1.52(e)(1)(iii) and 37 CFR §1.58, and is herein incorporated by reference in its entirety in accordance with 37 CFR §1.77(b)(4). The single ASCII (.txt) file for Table 2 via EFS-Web Filing, entitled "10324_Table_2.txt", which was created on 7 Mar. 2006, using a PC machine format, is 310 kb in size, and is Windows® compatible.

FIELD OF THE INVENTION

The present invention relates to the three dimensional coordinates of HIF-1 alpha-prolyl hydroxylase (EGLN1) and methods of identifying compounds for regulating activities regulated by hypoxia inducible factor 1 (HIF-1), including, but not limited to, erythropoiesis, iron transport, matrix remodeling and glucose utilization. The invention also relates to methods for the treatment of ischemia related disorders using compounds identified using the present invention.

BACKGROUND OF THE INVENTION

Hypoxia inducible factor (HIF) is a transcriptional complex that plays a key role in mammalian oxygen homeostasis and regulates angiogenic genes such as VEGF. The subunit components, HIF-1 alpha and HIF-1 beta (ARNT), are constitutively expressed and regulation is achieved by the selective destruction of HIF-1 alpha. HIF-1 alpha is a regulatory point of cellular response to hypoxia.

In the presence of oxygen, posttranslational modification by prolyl hydroxylation in the oxygen-dependent degradation domain (ODD) targets HIF-1 alpha subunits for proteasomal degradation via binding to the VHL (von Hippel-Lindau tumor suppressor protein), Elongin C/B, Cul2, Rbx1 ubiquitin E3 ligase complex. However, during ischemia, the hydroxylation of HIF-1 alpha is inhibited and HIF-1 alpha binds to ARNT to form a functional transcriptional activator that turns on genes with hypoxic response elements (e.g. VEGF, EPO, glycolytic enzymes). Proline hydroxylation of HIF-1 alpha is a required step for ubiquitinylation by the E3 ligase complex and is accomplished by three recently described enzymes, EGLN1, EGLN2, and/or EGLN3.

EGLNs are HIF-specific enzymes, distinct from procollagen prolyl-4-hydroxylases (P4H), which are responsible for the formation and stabilization of the triple helical domains in proteins, such as procollagen. EGLNs are human homologs of *Caenorhabditis elegans* Egl9 prolyl hydroxylase, and have been identified as HIF prolyl hydroxylases. EGLNs require molecular oxygen, iron, and oxoglutarate for activity. Furthermore, their activities are modulated by graded hypoxia and iron chelation and are inhibited by the prolyl hydroxylase inhibitors.

HIF prolyl hydroxylases belong to a family of non-heme iron Fe(II)-dependent oxygenases. HIF prolyl hydroxylases further differentiate into a class of dioxygenases with a requirement for 2-oxoglutarate (2-OG). Structural and mechanistic studies suggest that in the presence of dioxygen a catalytic process occurs in which a Fe:O species is generated during oxidative decarboxylation of 2-OG to succinate. This step is coupled to the oxidation of the substrate, which in the case of HIF, is a proline residue. The reaction results in the generation of succinate and $CO_2$ with oxygen incorporated into the hydroxyl group. Fe(II) is coordinated into the catalytic site of the dioxygenases and 2-OG is ligated to the iron. Iron may be displaced or replaced by other metals such as cobalt ions and render the enzyme inactive. However, further studies into understanding the mechanisms of action have been hampered by the lack of three-dimensional coordinates of EGLNs. The availability of such spatial coordinates may be useful in designing novel ligands or identifying other ligands of EGLNs, which may, in turn, be regulators of HIF-1 alpha-prolyl hydroxylation, which may, in turn, be useful in the treatment of HIF-regulated disorders.

SUMMARY OF THE INVENTION

The present invention provides three-dimensional coordinates of the catalytic domain of human EGLN1, and means to design and identify ligands of EGLNs, which may, in turn, be regulators of HIF-1 alpha-prolyl hydroxylation, which may be useful in the treatment of HIF-regulated disorders.

In one aspect, the invention relates to a crystal of a protein-ligand complex comprising a protein-ligand complex of an EGLN1 catalytic domain and a ligand, wherein the crystal effectively diffracts X-rays for the determination of the atomic coordinates of the protein-ligand complex to a resolution of greater than about 5.0 Angstroms; and wherein the EGLN1 catalytic domain comprises amino acids 1 to 248 of SEQ ID NO: 11, or an amino acid sequence that differs from amino acids 1 to 248 of SEQ ID NO: 11 by conservative substitutions.

In another aspect, the invention relates to the above-described crystal, wherein the ligand is [(1-Chloro-4-hydroxy-isoquinoline-3-carbonyl)-amino]-acetic acid.

In another aspect, the invention relates to the above-described crystal having unit cell dimensions of a=111±1 Å, b=111±1 Å, and c=40±1 Å, α=90°, β=90°, γ=120° in the space group $P6_3$ (hexagonal).

In another aspect, the invention relates to a method for identifying a compound useful in the treatment of a HIF-regulated disorder, comprising: using a three-dimensional structure of the EGLN1 catalytic domain as defined by its atomic coordinates; employing said three-dimensional structure to design, modify, or select a compound that binds EGLN1 in silico, and identifying the compounds that bind EGLN1 as compounds useful in the treatment of a HIF-regulated disorder.

In another aspect, the invention relates to a method for identifying a compound useful in the treatment of a HIF-regulated disorder, comprising: using a three-dimensional structure of the EGLN1 catalytic domain as defined by its atomic coordinates; generating a computational model of the EGLN2 or the EGLN3 catalytic domain based on the atomic coordinates of the EGLN1 catalytic domain; employing said three-dimensional structure to design, modify, or select a compound that binds EGLN2 or EGLN3 in silico, and identifying the compounds that bind EGLN2 or EGLN3 as compounds useful in the treatment of a HIF-regulated disorder.

In another aspect, the invention relates to a method for identifying a compound useful in the treatment of a HIF-regulated disorder, comprising: providing an EGLN1 catalytic domain crystal; exposing the crystal to a compound in a medium to form a crystal/compound complex; irradiating the exposed crystal with X-rays to generate a diffraction pattern; capturing the pattern to a recording device to generate diffraction data; processing the data to solve the structure of the complex; and determining the location and binding geometry of the compound within the structure of the complex; wherein the compound binding to one or more binding sites of EGLN1 catalytic domain, indicates that the compound is useful in the treatment of a HIF-regulated disorder.

In one aspect of the above-described methods, where applicable, the compound is designed de novo.

In another aspect of the above-described methods, where applicable, the compound is designed from a known chemical entity or a fragment.

In another aspect of the above-described methods, where applicable, the invention further relates to selecting a compound that has been shown to bind to an EGLN protein in silico; determining if the compound binds or regulates the EGLN in an in vitro, in vivo, or ex vivo assay; and identifying those compounds that bind or regulate EGLN1 as compounds useful for the treatment of an HIF-regulated disorder.

In another aspect of the above-described methods, where applicable, detecting the ability of the compound for binding or regulating an EGLN, is performed using an enzymatic assay.

In another aspect of the above-described methods, where applicable, detecting the ability of the compound for binding or regulating an EGLN, is performed using a cell-based assay.

DESCRIPTION OF SEQUENCE LISTING

Figure 1A:
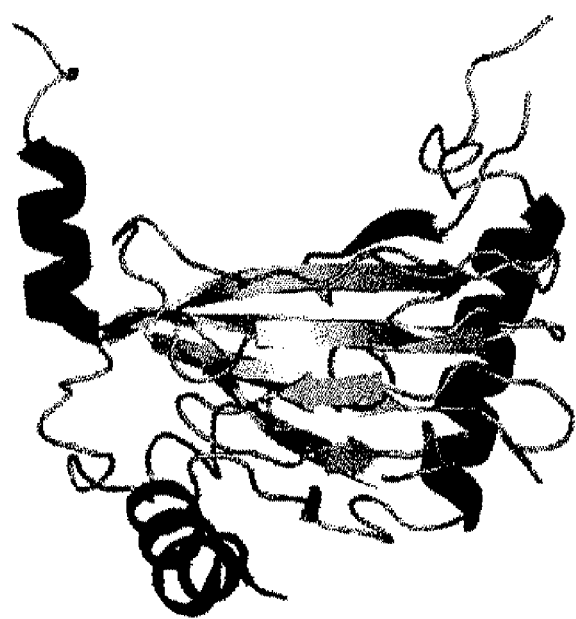
FIG. 1A—side view, FIG. 1B—top view.

Variously tagged human EGLN1 catalytic domain (EGLN1-CD), primers used for constructing vectors containing EGLN1-CD fragment, nucleic acid and protein sequences of the catalytic domain, and protein sequences of full-length EGLN1, EGLN2, and EGLN3, are listed with their corresponding SEQ ID NOs. in Table 1 and are disclosed in the appended Sequence Listing provided as a ".txt" file.

TABLE 1

| Sequence Name | SEQ ID NO: |
|---|---|
| TVMV-EGLN1, amino acids 179-426 | 1 |
| His-TVMV-EGLN1, amino acids 179-426 | 2 |
| His-EGLN1, amino acids 179-426 | 3 |
| Primer 1 | 4 |
| Primer 2 | 5 |
| Primer 3 | 6 |
| Primer 4 | 7 |
| Primer 5 | 8 |
| Primer 6 | 9 |
| EGLN catalytic domain, amino acids 179-426, coding sequence | 10 |
| EGLN catalytic domain, amino acids 179-426, protein sequence | 11 |
| EGLN1, Genbank Accession No. NM_022051 | 12 |
| EGLN2, Genbank Accession No NM_053046 | 13 |
| EGLN3, Genbank Accession No NM_022073 | 14 |

DETAILED DESCRIPTION OF THE INVENTION

The invention relates to identifying or designing compounds useful for regulating EGLN1 activity. The crystal structure information presented herein may be useful in designing compounds and modeling them or their potential interactions with binding site(s) of EGLN1. Actual compounds may be identified from following design and model work performed in silico. A compound identified using the present invention may be effective for the treatment of a HIF-regulated disorder.

The coordinates shown in Table 2 [SEQ. ID NO: 1] (submitted as an appendix on a compact disc, as described above); provide a measure of atomic location in Angstroms, to a first decimal place. The coordinates are a relative set of positions that define a shape in three dimensions. An entirely different set of coordinates having a different origin and/or axes may define a similar or identical shape. However, varying the relative atomic positions of the atoms of the structure so that the root mean square deviation of the conserved residue backbone atoms (i.e. the nitrogen-carbon-carbon backbone atoms of the protein amino acid residues) is less than 1.5 Å, when superimposed on the coordinates provided in Table 2 for the conserved residue backbone atoms, may generally result in structures which are substantially the same as the structure defined by Table 2 in terms of both its structural characteristics and its usefulness for structure-based drug design. Similarly, changing the number and/or positions of the water molecules of Table 2 may not generally affect the usefulness of the structure for structure-based drug design. Thus, it is within the scope of the invention if: the coordinates of Table 2 are transposed to a different origin and/or axes; the relative atomic positions of the atoms of the structure are varied so that the root mean square deviation of conserved residue backbone atoms is less than 1.5 Å, when superimposed on the coordinates provided in Table 2 for the conserved residue backbone atoms; and/or the number and/or positions of water molecules is varied. References herein to the coordinates of Table 2, thus includes the coordinates in which one or more individual values of the Table 2 are varied in this way.

Due to the degeneracy of nucleotide coding sequences, other DNA sequences that encode substantially the same amino acid sequence as an EGLN1 catalytic domain or full-length EGLN gene may be used in the practice of the present invention. These include but are not limited to allelic genes, homologous genes from the same species, e.g., EGLN2 or EGLN3, homologous genes from other species, and nucleotide sequences comprising all or portions of EGLN1 or other EGLN genes. In addition, modifications in the EGLN1 crystal structure due to e.g. mutations, additions, conservative and non-conservative substitutions, and/or deletions of amino acid residues may account for variations in the EGLN1 atomic coordinates. However, atomic coordinate data of thus modified EGLN1, so that a ligand that bound to one or more binding sites of the EGLN1 binding pocket would also be expected to bind to the corresponding binding sites of the modified EGLN1, are within the scope of the invention. In one aspect, such modified coordinate data define at least one EGLN1 binding site.

In Silico Drug Design

The present invention permits the use of virtual design techniques (i.e., computer modeling or "in silico") to design, select, and synthesize compounds capable of regulating EGLN1. In turn, these compounds may be effective in the treatment of a HIF-regulated disorder.

In addition to the more traditional sources of test compounds, computer modeling and searching technologies permit the rational selection of test compounds by utilizing structural information from the ligand binding sites of proteins of the present invention. Such rational selection of compounds may decrease the number of compounds that may need to be screened to identify a therapeutic candidate compound. Knowledge of the protein sequences of the present invention may allow for generation of models of their binding sites that may be used to screen for potential ligands. This process may be accomplished with the skills known in the art. One approach involves generating a sequence alignment of the protein sequence to a template (derived from the crystal structures or NMR-based model of a similar protein(s), conversion of the amino acid structures and refining the model by molecular mechanics and visual examination. If a strong sequence alignment may not be obtained, then a model may also be generated by building models of the hydrophobic helices. Mutational data that point towards contact residues may also be used to position the helices relative to each other so that these contacts are achieved. During this process, docking of the known ligands into the binding site cavity within the helices may also be used to help position the helices by developing interactions that may stabilize the binding of the ligand. The model may be completed by refinement using molecular mechanics and loop building using standard homology modeling techniques. General information regarding modeling may be found in Schoneberg, T. et. al., *Molecular and Cellular Endocrinology*, 151:181-193 (1999), Flower, D., *Biochim Biophys Acta*, 1422, 207-234 (1999), and Sexton, P. M., *Curr. Opin. Drug Discovery and Development*, 2, 440-448 (1999).

Once the model is completed, it may be used in conjunction with one of several computer programs to narrow the number of compounds to be screened, e.g., the DOCK program (UCSF Molecular Design Institute, San Francisco, Calif. 94143) or FLEXX (Tripos Inc., MO). One may also screen databases of commercial and/or proprietary compounds for steric fit and rough electrostatic complementarity to the binding site.

In Silico Screening of Compounds

In one aspect, the invention provides means to carry out virtual screening of compounds using the disclosed atomic coordinates or coordinates derived therefrom.

The atomic coordinates of the three-dimensional structure elucidated by the invention are input into a computer so that images of the structure and various parameters are shown on the display. The resultant data are input into a virtual compound library. Since a virtual compound library is contained in a virtual screening software, the above-described data may be input into such a software. Compounds may be searched for, using a three-dimensional structure database of virtual or non-virtual compounds, such as MDDR (Prous Science, Spain).

The potential interactions of a compound may be analyzed prior to its actual synthesis and testing by the use of computer modeling techniques. If the theoretical structure of the given compound suggests insufficient interactions with EGLN1, synthesis and testing of the compound may be obviated. However, if computer modeling indicate sufficient interactions, the molecule may then be synthesized and tested for its ability to regulate EGLN1, using various methods described herein and/or that are known to a person skilled in the art.

Compounds may be computationally evaluated and designed by means of a series of steps in which chemical entities or fragments are screened and selected for their ability to bind with individual binding sites or combinations thereof (e.g., P0, P+1, P−1) or other areas of EGLN1.

One skilled in the art may use any of several methods to screen chemical entities or fragments for their ability to bind to EGLN1 and more particularly with the specific binding sites. Sequences of EGLN2 (SEQ ID NO: 13) or EGLN3 (SEQ ID NO: 14), may also be threaded onto the protein backbone of the EGLN1 catalytic domain derived from the crystal structure, with side chain positions optimized using methods known in the art. The resulting structural models may then be used to discover chemical entities or fragments that regulate EGLN1, EGLN2, or EGLN3 via in silico docking. The process may begin by visual inspection of, for example, the active site on the computer screen based on the EGLN1 coordinates presented in Table 2. Selected fragments or chemical entities may then be positioned in a variety of orientations, or docked, within a binding site of EGLN1. Docking may be accomplished using software such as QUANTA™, SYBYL™, followed by energy minimization and molecular dynamics with molecular mechanics forcefields softwares, such as CHARMM™ and AMBER™.

Specialized computer programs may also assist in the process of selecting fragments or chemical entities. These include, but are not limited to, GRID™ (Goodford, P. J., J. Med. Chem., 28, 849-857 (1985)); MCSS™ (Miranker, A. and M. Karplus, "Proteins: Structure, Function and Genetics, 11, 29-34 (1991)); (3) AUTODOCK™ (Goodsell, D. S. and A. J. Olsen, Proteins: Structure, Function, and Genetics, 8, 195-202 (1990; DOCK™ (Kuntz, I. D. et al., J. Mol. Biol., 161, pp. 269-288 (1982)); GLIDE™ (Schrodinger Inc.); FLEXX™ (Tripos Inc); (7) GOLD™ (Jones et al., J. Mol. Biol., 245, 43-53, 1995).

Once suitable chemical entities or fragments have been selected, they may be assembled in silico or synthesized into a single compound. Chemical syntheses may be carried out by methods known in the art. In silico assembly may proceed by visual inspection of the relationship of the fragments to each other on the three-dimensional image displayed on a computer screen in relation to the structure coordinates of EGLN1. This may be followed by manual model building using softwares such as QUANTA™ or SYBYL™.

Useful programs for connecting the individual chemical entities or fragments include the following: CAVEAT™ (Bartlett, P. A. et al, Royal Chem. Soc., 78, 182-196 (1989)); 3D Database systems such as MACCS-3D™ (MDL Information Systems, San Leandro, Calif.); and HOOK™ (Molecular Simulations, Burlington, Mass.).

In addition to building a compound in a step-wise fashion as described above, compounds may be designed as a whole or "de novo" using an empty active site or optionally including some portion(s) of a known compound. Such methods include, but are not limited to, LUDI™ (Bohm, H.-J., J. Com R. Aid. Molec. Design, 6, pp. 61-78 (1992)); LEGEND™ (Nishibata, Y. and A. Itai, Tetrahedron, 47, p. 8985 (1991)), and LEAPFROG™ (Tripos Inc., St. Louis, Mo.).

Once a compound has been designed or selected, the efficiency with which that compound may regulate EGLN1 may be tested and optimized by computational evaluation. For example, a compound may demonstrate a relatively small difference in energy between its bound and unbound states (i.e., a small deformation energy of binding). A compound may interact with EGLN1 in more than one conformation that is similar in overall binding energy. In those cases, the deformation energy of binding is taken to be the difference between the energy of the unbound compound and the average energy of the conformations observed.

A compound that is designed or selected may be further computationally optimized so that in its bound state it may lack repulsive electrostatic interactions. Such interactions include repulsive charge-charge, dipole-dipole, and charge-dipole interactions. The sum of all electrostatic interactions between the compound and EGLN1, may make a neutral or favorable contribution to the enthalpy of binding. Software programs to evaluate compound deformation energy and electrostatic interaction include, e.g., Gaussian 92™ (M. J. Frisch, Gaussian, Inc., Pittsburgh, Pa.); AMBER™ (P. A. Kollman, University of California at San Francisco, Calif.); QUANTA/CHARMM™ (Molecular Simulations, Inc., Burlington, Mass.); and Insight II/Discover™ (Biosysm Technologies Inc., San Diego, Calif.).

Once a compound has been optimally selected or designed, substitutions may be made in some of its atoms or side groups in order to improve or modify its binding properties. Initial substitutions may be conservative, i.e., the replacement group will have approximately the same size, shape, hydrophobicity and charge as the original group. Such substituted compounds may then be analyzed for efficiency of fit to EGLN1 by software programs similar to those described.

Crystallographic Evaluation of Chemical Entities for Binding to EGLN1

The invention allows one skilled in the art to study the binding of compounds to EGLN1 by exposing either individual compounds or mixtures of compounds (such as may be obtained from combinatorial libraries) into EGLN1 crystals or, alternatively, by co-crystallization of the compounds of interest with EGLN1, using methods known in the art, and those described in the Examples herein. Acquisition and analysis of X-ray diffraction data from these crystals may then be performed using standard methods. If a compound binds to EGLN1 then positive difference electron density will be observed in the Fourier maps calculated using the X-ray diffraction intensities and phases obtained from the EGLN1 model presented herein. Models of the chemical entities may then be built into the electron density using standard methods, and the resulting structures may be refined against the X-ray diffraction data, providing experimental data describing the interaction of the compounds of interest. Those skilled in the art may use these models to design compounds based either on purely structural data; or on combination of structural data, biological/chemical activity based structure-activity relationship, and in silico drug design.

The compounds that are thus designed or selected may further be tested in an in vitro, in vivo, or ex vivo assays to determine if they regulate EGLNs. Such assays are known to one skilled in the art, e.g., WO 02/074980, US 2002/0192737, and WO 03/028663, all of which are incorporated herewith in their entirety.

Treatment of HIF-Regulated Disorders

The present invention (three-dimensional coordinates of EGLN1) and compounds that are identified using these coordinates may be used in a method for the treatment of an HIF-1 alpha regulated disorder. The term "regulate" is defined as in its accepted dictionary meanings. Thus, meaning of the term "regulate" includes, but is not limited to, up-regulate or down-regulate, to fix, to bring order or uniformity, to govern, or to direct by various means.

Therapeutic Effects of EGLN Inhibition and HIF Stabilization

Inhibition of an EGLN may stabilize the expression of HIF-1 alpha. In a setting of hypoxia, when EGLN is inhibited, HIF expression and activity may be enhanced and may be manifested in the regulation of genes involved in a variety of processes including the regulation of blood flow (VEGF, VEGR1 and angiopoietin 2), metabolism (enolase, phosphofructokinase, aldolase) and oxygen delivery (erythropoietin) (Semenza, Biocehm Pharmacol, 64, 993-998 (2002)). Modulation of these processes may contribute to the therapeutic effects of HIF stabilization. Thus, the inhibition of EGLN in a setting of ischemia may produce therapeutic benefits from a combination of effects derived from several different physiological processes. Such processes may include, but are not limited to, increasing blood flow, increasing oxygen delivery, and improving myocardial efficiency.

Increasing Blood Flow

Administration of PR39 peptide, a proteasome inhibitor that blocks HIF-1 alpha degradation, in the heart enhanced myocardial blood flow and increased myocardial vascularity in normal myocardium and in the peri-infarct zone following coronary artery ligation (Li et al, Nat Med, 6, 49-55 (2000)). Recently, the angiogenic potential of prolyl hydroxylase inhibition was demonstrated when inhibitors of prolyl-4-hydroxylase (L-mimosine, ethyl-3,4 dihydroxybenzoate, S956711) were shown to induce HIF protein in HT1080, PC12W and 3T3L1 cells in culture. When administered to rats, L-mimosine and S956711 induced HIF protein expression in the kidney. Several other studies suggest that stabilization of HIF could enhance tissue vascularity and collateral blood flow. Transgenic mice expressing a constitutively active HIF-1 alpha in the skin had increased dermal vascularity. Although these mice had a 13-fold increase in VEGF levels, there was no sign of edema, inflammation, or vascular leakage, all of which occurred in transgenic mice overexpressing VEGF alone in the skin (Elson et al, Genes Dev, 2520-2532 (2001)). Similarly, expression of a constitutively active HIF-1 alpha/VP16 fusion protein in a rabbit model of hind limb ischemia increased VEGF expression and improved multiple parameters of collateral function including distal blood pressure, collateral blood flow, angiographic score and capillary density (Vincent et al, Circ, 102, 2255-2261 (2000)). Taken together, these data suggest that HIF-1 alpha stabilization may enhance the vascularity and improve blood flow in multiple tissues and provide support for targeting HIF-1 alpha for proangiogenic therapy.

Increasing Oxygen Delivery

In addition to angiogenesis, stimulating erythropoiesis offers another means of delivering more oxygen to tissues. Anemia is an independent risk factor for mortality in patients with LV dysfunction and severe heart failure. In patients with LV dysfunction, decreased renal function is also an independent risk factor for mortality, more so if concurrent with anemia. Furthermore, in a limited study involving 26 anemic patients with chronic heart failure, administration of erythropoietin (3 times/week) significantly improved exercise capacity that was coupled to increases in hemoglobin and peak oxygen consumption (Mancini et al, Cric, 107, 294-299 (2003)).

Improving Myocardial Efficiency

In heart failure, the switch from oxidative phosphorylation to glycolysis has been described as an adaptive mechanism for energy production in the face of ischemic conditions. With several key glycolytic enzymes regulated by HIF, therapeutic benefits may be derived from activation of this metabolic process. In one study, treatment of human and rodent cells in culture induced HIF-regulated genes such as GLUT1 and LDH (Warnecke et al, FASEB J, 17, 1186-1188 (2003)). In another study, ethyl-3,4-dihydroxybenzoate and dimethyloxalylglycine both induced the expression GLUT1, heme oxygenase and nitric oxide synthase in neonatal rat cardiomyocytes. Furthermore, inhibitor treatment increased myocyte survival in the presence of metabolic inhibitors, cyanide and 2-deoxyglucose (Wright et al, J Biol Chem, 278, 20235-20239 (2003)).

Examples

1. Cloning of the Catalytic Domain of EGLN1

The catalytic domain of EGLN1, amino acids 179 to 426 (SEQ ID NO: 11), is amplified from a commercially available cDNA clone using PfuUltra® DNA polymerase (Stratagene) in two PCR™ reactions—the first one uses the cDNA clone as a template, amplified with primers (SEQ ID NOs: 4 and 5), the second one uses the product of the first one as template, amplified with primers (SEQ ID NOs: 6 and 7). The resulting amplicon is flanked by AttB sites for Gateway® (Invitrogen) recombination-based cloning. The sequence between the AttB sites encodes for a Tobacco Vein Mottling Virus (TVMV) protease cleavage site (amino acid residues ETVR-FQS) followed by residues 179 to 426 of EGLN1 (SEQ ID NO: 1).

This amplicon is gel-purified and used in a BP recombination reaction with pDONR-221 vector (Invitrogen), following manufacturer's instructions: a 10-μl reaction contains 100 ng of purified amplicon, 150 ng of pDONR-221 supercoiled plasmid, reaction buffer, Tris-EDTA buffer (pH 8.0), and 2 μl of BP clonase. The reaction is incubated at room temperature for 2 hours and then digested with Proteinase K for 10 minutes at 37° C. An aliquot of chemically competent OneShot® TOP 10 E. coli cells (Invitrogen) is transformed with 2 μl of the digested reaction mixture as per manufacturer's instructions. BP recombinants are selected by plating the transformation overnight on LB-Agar plates supplemented with 50 mg/L Kanamycin. Several single colonies are picked, and the bacteria are grown overnight in 3-5 ml aliquots of LB+0.4% glucose+50 mg/L Kanamycin. Plasmid DNA is prepared from these bacterial cultures using a Miniprep kit (Qiagen). Sequencing may be used to confirm that the BP recombination products have been made correctly. The products are designated as pENTR-TVMV-EGLN1-179-426. A single Entry vector is selected for the next step of the Gateway reaction—instead of the AttB sites; it carries the AttL sites, flanking the same region as described earlier for the PCR amplicon.

The Entry vector pENTR-TVMV-EGLN1-179-426 is recombined with an in-house Gateway Destination vector pET45-DEST that is derived from a commercial pET45 vector through insertion of a Gateway cassette into a blunt restriction site, according to manufacturer's instructions. The LR recombination reaction is set up: 125 ng of pENTR-TVMV-EGLN1-179-426 is mixed with 130 ng of pET45-DEST, TRIS-EDTA buffer (pH 8.0), and 1 μl of LR clonase II (Invitrogen). The reaction is allowed to proceed for 3 hours at 22° C. and then digested with Proteinase K for 10 minutes at 37° C. An aliquot of chemically competent OneShot® BL21 (DE3) E. coli cells (Invitrogen) is transformed with 3 μl of the digested reaction mixture as per manufacturer's instructions. Transformed cells are plated on LB-Agar plates supplemented with 100 mg/L Carbenicillin and 1% glucose. Several single colonies are tested using colony-PCR with primers 1 and 2 to establish the correct transfer of the genetic material from the Entry to the Destination vector. The resulting expression vector encodes a His-tagged, TVMV-cleavable construct His-TVMV-EGLN1-179-426 (SEQ ID NO: 2). Several colonies are grown in LB+0.8% glucose+100 mg/L Carbenicillin, and glycerol stocks are prepared.

To create a linker-less His-EGLN1-179-426 clone, plasmid DNA is prepared from one of the colonies above and used as a template in QuikChange® mutagenesis (Stratagene) as described in the manufacturer's manual: a 50-μl reaction contains 2.5 U of PfuUltra DNA polymerase in manufacturer's buffer, 20 ng of template plasmid, and 125 ng each of mutagenic primers ((SEQ ID NOs: 8 and 9)). PCR is run as follows: 2 minute at 97° C., followed by 20 cycles each consisting of 30 seconds at 97° C., 30 seconds at 55° C., and 7 minutes at 68° C. The final extension cycle is conducted at 68° C. for 15 minutes. The PCR reaction is digested with 30 units of DpnI polymerase for 2 hours at 37° C., and a 2 μl aliquot is transformed into chemically competent OneShot® TOP E. coli cells. Cells are plated on LB-Agar plates supplemented with 100 mg/L Carbenicillin. Single colonies are picked, grown in LB+100 mg/L Carbenicillin, and plasmid DNA is sequenced. DNA from one of the sequence-confirmed colonies is used to transform chemically competent OneShot® BL21 (DE3) E. coli cells (Invitrogen), plated and grown as described above for the LR reaction products. The resulting product His-EGLN1-179-426 contains no extra residues between the His-tag and the EGLN1 catalytic domain (Sequence 3). Single colony outgrowths are used to prepare glycerol stocks.

2. Expression Studies of EGLN1-179-426 Constructs

A glycerol stock is used to inoculate a starter culture in Terrific Broth II (TB-II, Q-Biogene)+0.8% glucose+1.6% glycerol, in a shaking incubator at 37° C. grown overnight to $A_{600}$ of 5.0-7.0. Several media are scouted for best expression—including TB, LB, and M9. The effects of carbon source are studied by supplementing the media with glycerol (1.6%) and/or glucose (0.8%). Aliquots of the starter culture are diluted into 5 ml of fresh media to $A_{600}$ of 0.1-0.2 and are allowed to grow at the 37° C. until their $A_{600}$ reaches ~1.0. At that point, temperature is shifted to the desired value (15° C., 22° C., or 37° C.) and protein production is induced by adding a desired amount of either IPTG (0.1, 0.5, 1.0 mM final concentration) or Lactose (0.2, 0.5, 1.0% final concentration). Cells are harvested by centrifugation (5000 g) at a time point that is dependent on growth temperature: 37° C.—4 hours, 30° C.—6 hours, 22° C.—18 hours post-induction, and stored at −80° C.

Cells are lysed by resuspending them in 1 ml of the lysis cocktail containing 70% B-PER, 30% Y-PER (Pierce) buffers supplemented with EDTA-free protease inhibitors (Roche), 0.1 mg/ml lysozyme (Sigma), 0.05 mg/ml DNAse I (Sigma), and 10 mM imidazole. Lysis is allowed to proceed for 5 minutes at room temperature. Lysates are clarified by centrifugation (5 minutes at 16000 g). Supernatants are passed through 50-μl Ni-NTA in disposable 1-ml columns. The resin is washed twice with 1 ml of the following buffer: Tris pH 7.8, 250 mM NaCl, 10 mM imidazole, followed by elution with 50 ul of the same buffer supplemented with 200 mM imidazole.

Eluates are analyzed by SDS-PAGE with Coomassie G-250 staining. The best expression conditions are inferred from thickness and densitometric analysis of the band at the right molecular weight.

Based on the results of the scouting protocol represented above, the best expression conditions for His-TVMV-EGLN1-179-426 and His-EGLN1-179-426 constructs are: TB-II+1.6% glycerol+0.8% glucose, induced with 0.5-1.0 mM IPTG at 22° C. overnight. These conditions are successfully scaled up for fermentation.

3. Fermentation of EGLN1-179-426 Constructs

A 50-ml of starter culture (TB-II+1.6% glycerol+0.8% glucose+100 mg/L Carbenicillin) is inoculated from a glycerol stock. The culture is allowed to grow overnight at 37° C. with shaking. A 2 L glass vessel, Rushton impeller-equipped Biostat-MD fermenter is loaded with the same medium and pre-equilibrated to 37° C. The fermenter is inoculated with the starter culture so that the resulting $A_{600}$ is ~0.05. Fermentation is conducted using a 2.5 L/min airflow, 700 rpm stirring speed in a pH-stat mode (equilibrium pH 7.3) using phosphoric acid and sodium hydroxide solutions to maintain the pH. After 5-6 hours the culture reaches $A_{600}$ of ~9-11 and dissolved oxygen concentration ($dO_2$) drops to below 5% (100% is set as the $dO_2$ of the media fully equilibrated with air). At this point, an additional 0.5% glycerol and 0.2% glucose are added to the fermenter and protein expression is induced by adding 1 mM IPTG. The stirring speed and airflow are allowed to adjust to maintain oxygenation above 5%—regardless of the $dO_2$ the stirring speed and air flow are not reduced below 600 rpm and 2 L/min, respectively. Concomitantly, the temperature is shifted to 22° C. Fermentation is allowed to proceed in this fashion for 16-18 hours at which point the cells are harvested by centrifugation (5000 g, 15 minutes) and frozen at −80° C. The cell mass is whitish-gray due to accumulation of protein inclusion bodies in bacterial cells. Wet cell mass yield is 100-150 g, which may be further increased utilizing fed-batch or continuous feed fermentation strategies.

4. Purification of His-EGLN1-179-426

Lysis of 100 g of cell mass is conducted by homogenization (at 4° C.) into 200 ml of the lysis cocktail: B-PER® reagent (Pierce)—80%, Y-PER® reagent (Pierce)—20% supplemented with 50 mg bovine DNAse-I (Sigma), 50 mg hen egg lysozyme (Sigma), 10 mM imidazole, 2 mM PMSF, 0.1 mM AEBSF, and 5 mM benzamidine. Lysis is allowed to proceed for 20 minutes at 4° C. following complete breakdown of the bacterial pellet. Lysate is clarified by centrifugation (25,000 g for 30 minutes) and the pellet is discarded.

Lysate is passed through a 30-ml Ni-affinity resin (His-Select®, Sigma) at a flow rate of 5 ml/min, using an AKTA-Explorer® liquid chromatography system. The column is washed with at least 150 ml of 25 mM TRIS-HCl pH 7.8, 250 mM NaCl, 10 mM imidazole until optical absorption at 280 nm reaches a plateau. Bound proteins are eluted with a linear gradient from 10 to 200 mM imidazole in the same buffer. Fractions are collected and analyzed by SDS-PAGE and MALDI-TOF MS. Mass spectroscopy reveals a complete loss of the initiator methionine. The relevant fractions are pooled and concentrated to 6 mg/ml according to the theoretical value of $A_{280}$ in 6M guanidine (1.3 OD units per mg/ml solution in a 1-cm optical path). Concentrated protein is flash-frozen in liquid nitrogen and stored at −80° C. A typical yield of pure protein is 150 mg per 100 g of cell mass used.

5. Crystallization

For initial crystallization experiments, His-EGLN1-179-426 is buffer-exchanged (via dilution and concentration using a spin-filter device) into a variety of buffers together with a number of different compounds. The protein is concentrated to ~10 mg/ml and 2+2 µl hanging drops (protein: reservoir) are set up against a standard set of sparse-matrix crystallization experiments utilizing commercial as well as custom screens (DeCode Genetics, Hampton Research, Jena Biosciences, Nextal Biotechnologies, etc.). First hits are obtained when protein is exchanged into a buffer consisting of 10 mM HEPES pH 7.0, 150 mM NaCl, 1 mM $NiSO_4$, and 0.1% n-octyl beta-glucoside and 1 mM compound X is added before the final concentration step. Several initial conditions are identified that are refined to the final set of crystallization well solutions containing 200-300 mM $(NH_4)_2SO_4$, 100 mM NaOAc pH 4.8-5.4, and 22-25% PEG-4000. Nucleation is usually seen in 1-2 days at 21° C. ultimately producing clusters of hexagonal rods that reach 0.07-0.15 mm in diameter in 2-4 more days. These conditions may be supplemented with 10-20% glycerol (or other additives), which results in slower growth but fewer (and larger) crystals per drop.

6. Data Collection

Crystals of EGLN1-179-426 may be cryoprotected by immersion into Paratone-N directly out of the crystallization drop. Flash freezing in a stream of nitrogen gas at 100K results in diffraction to 1.5-1.6 Å at the ID beam line of the SER-CAT, APS tuned to 1.0 Å X-ray radiation wavelength. Data is collected using a Mar-365 CCD, integrated, and scaled using HKL-2000. Several crystals are derivatized with various heavy-atom reagents. In particular, mercury and platinum derivatives are obtained by soaking crystals for 45 minutes in 0.1 mM $(EtOHg)_2OPO_2$ and 1.0 mM $K_2PtCl_6$, respectively. An additional platinum derivative is afforded by co-crystallization of the protein with 1 mM $K_2Pt(NO_2)_4$. Data from these three derivatives are collected to 2.7 Å, 1.9 Å, and 1.7 Å respectively.

7. Structure Solution and Refinement

The structure is solved by Multiple Isomorphous Replacement (MIR) using the native and the three derivative data sets. Initial phasing is done via the program SOLVE at 2.8 Å resolution and the map is of sufficient quality to allow semi-manual building of the polypeptide chain using the programs Coot and Quanta (Accelrys). Incorporation of higher-resolution data into the phasing solution by means of progressive density modification (program RESOLVE) allows one to assign most of the amino acid side-chains from the experimental electron density at 2.6 Å.

Progressive rounds of refinement (Refmac, CCP4) and rebuilding (Coot) result in the final model containing residues 188-405 of the protein, the $Fe^{2+}$ (or $Ni^{2+}$) ion, one molecule of compound X, and numerous water molecules, at 1.6 Å resolution. Final quality of the model is evaluated by ProCheck™ and SFCheck™ programs, and is found to be consistent with that of a high-quality protein structure.

Atomic coordinates of the complex between EGLN1 catalytic domain and compound is [(1-Chloro-4-hydroxy-isoquinoline-3-carbonyl)-amino]-acetic acid (as well as metal ion and numerous water molecules) are presented in the attached text file "10324_Table 2.txt". These coordinates may be visualized using a molecular graphics application capable of reading pdb-formatted files. Suitable applications include, e.g., RasMol™, Discovery Studios™ (Accelrys), PyMol™, Coot™, O™, Quanta™, SwissPDB Viewer™.

8. Structure of the Catalytic Domain of EGLN1

Of the residues 179-426 that are included in the vector construct, residues 188-410 are clearly defined by the model (with the exception of residues 263-271 that are disordered).

Figure 1B:
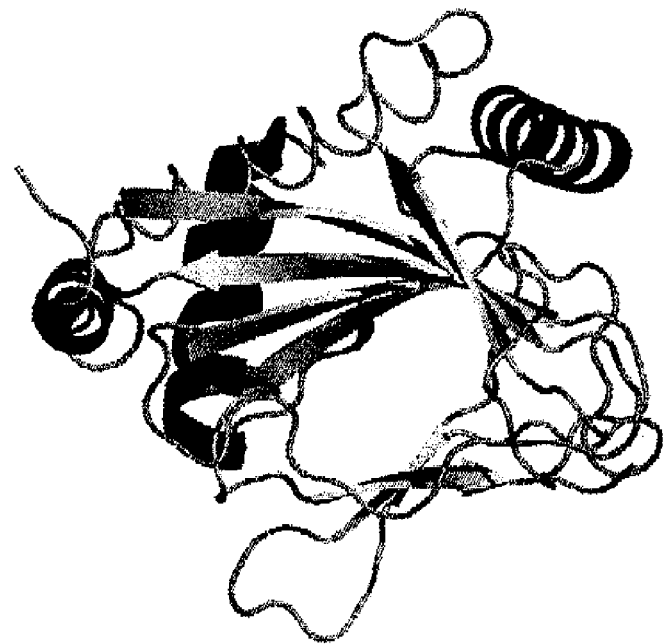
FIG. 1 shows overall fold of the EGLN1 catalytic domain.
Figure 2A:
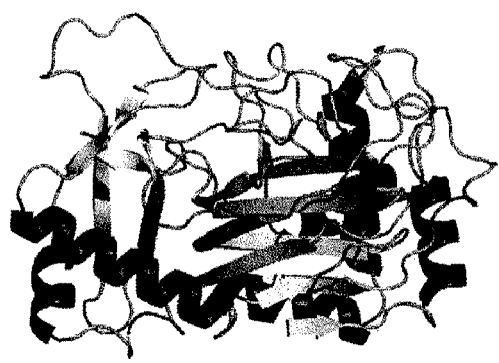
FIG. 2A clavulinic acid synthase (CAS), FIG. 2B deoxycephalosporin synthase (DAS), FIG. 2C asparaginyl hydroxylase (FIH), FIG. 2D isopenicillin synthase (IPNS), FIG. 2E P3H.
Figure 2B:
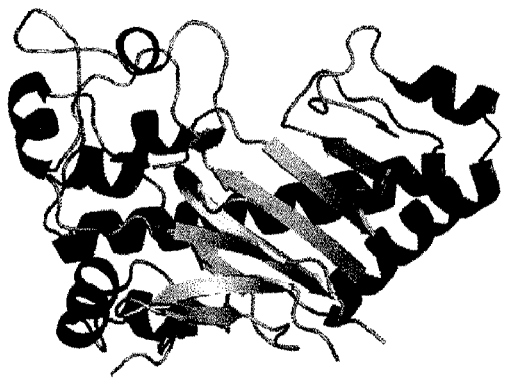
FIG. 2 shows overall folds of other members of the 2-OG-dependent oxygenase family.
Figure 2C:
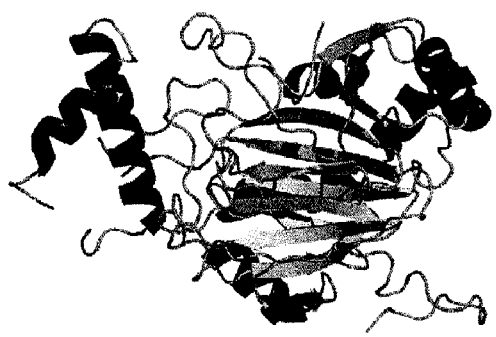
Figure 2D:
Figure 2E:
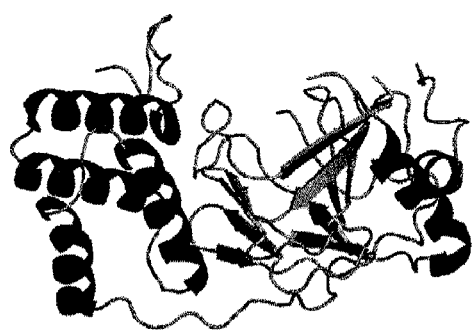

EGLN1 catalytic domain (EGLN1-CD) has a distorted jelly roll fold (beta-basket) composed of 11 beta-strands supported from one side by four alpha helices (FIG. 1). This beta-basket is a core fold of oxoglutarate-dependent oxygenases such as the deoxycephalosporin synthase (DAS), clavulinic acid synthase (CAS), asparaginyl hydroxylase (FIH), isopenicillin synthase (IPNS), or proline-3-oxygenase (P3H) (PDB IDs: 1RXF, 1DS0, 1H2K, 1BK0, 1E5S respectively). The similarity is only prominent in the core of the proteins where the structurally conserved beta-strand residues superimpose with Cα r.m.s.d. of 1.8-1.5 A, while the numbers and positions of alpha helices are not entirely conserved. Of the known OG-dependent oxygenase structures, EGLN1-CD has minimally decorated fold (FIG. 2).

Figure 3:
FIG. 3 shows a crystallographic trimer of EGLN1-CD with monomers shaded separately.

In the crystal, the EGLN1-CD molecules are arranged as trimers around the crystallographic threefold axis, so that the C-terminal residues of each molecule interact with its neighbor (FIG. 3).

Figure 4:
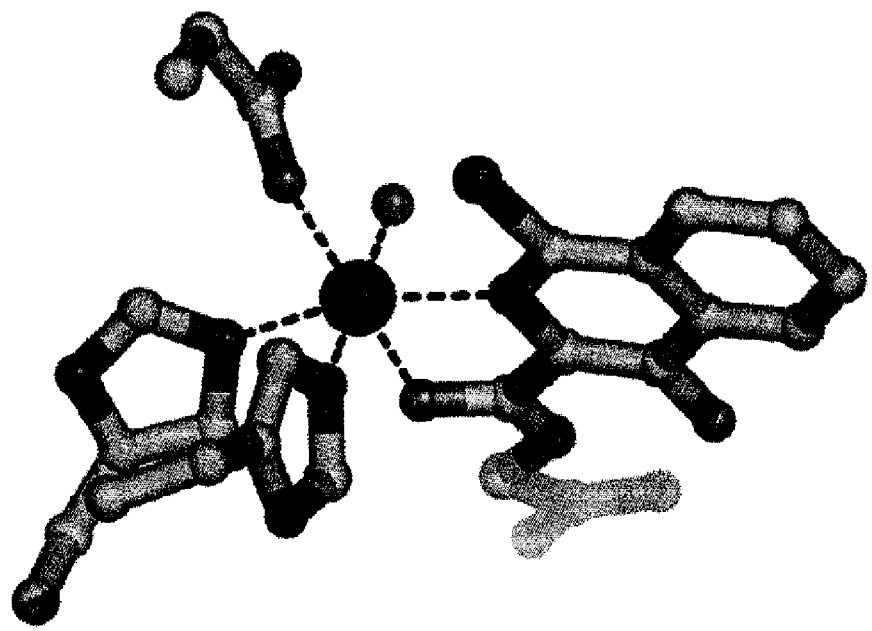
FIG. 4 shows the iron coordination sphere in the EGLN1 catalytic domain structure: Iron(II) is coordinated by the ligand, two histidine side chains, an aspartic acid side chain, and a water molecule.
Figure 5C:
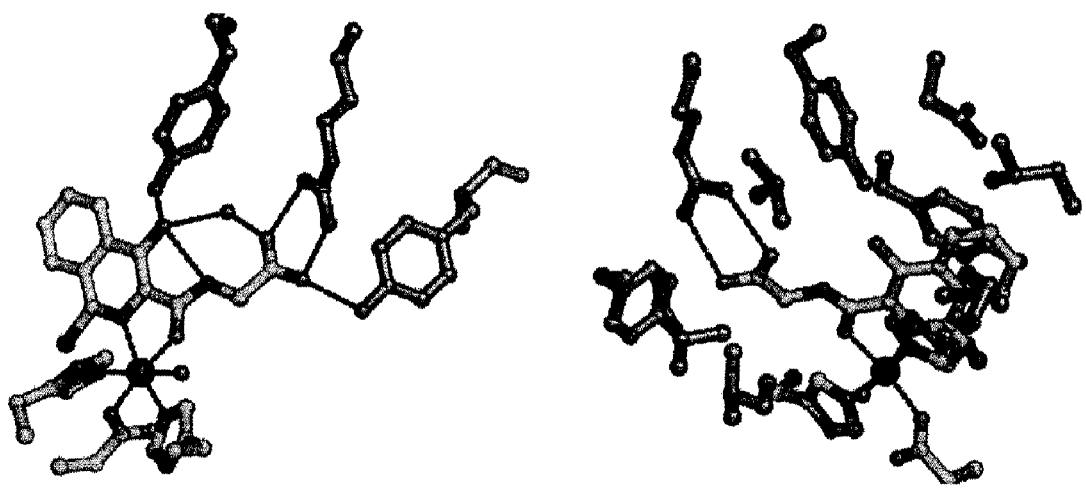
FIG. 5 shows the way compound [(1-Chloro-4-hydroxy-isoquinoline-3-carbonyl)-amino]-acetic acid occupies the active site of EGLN1.
FIG. 5A focuses on polar interactions, whereas FIGS. 5B and 5C highlight hydrophobic interactions between the ligand and the protein.
Figure 5C:
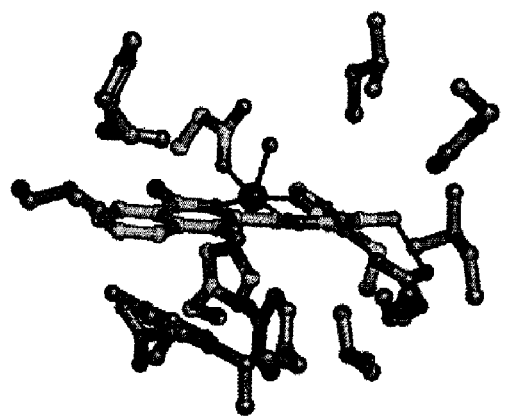

9. EGLN1 active site and binding of [(1-Chloro-4-hydroxy-isoquinoline-3-carbonyl)-amino]-acetic acid The active site of the enzyme is located at the wider end of the beta-basket. The catalytic Fe(II) ion has an octahedral ligand configuration. The metal ion is held in place by interactions with side chain atoms of a His-Asp-His triad (residues His-313, Asp-315, His-374), the ligand (bidentate), and a water molecule (FIG. 4). The first two members of the triad belong to the His-X-Asp motif characteristic of many non-heme oxygenases. The carboxymethylene amide portion of the ligand is embedded in a trough formed by the side chains of Leu-343, Gly-307, and Val-376. The carboxylic acid forms a tight ion pair with arginine-383 and a hydrogen bond with Tyr-329 hydroxyl. The chloro-isoquinoline ring system of the ligand interacts with hydrophobic side chains of Tyr-310, Met-299, Trp-389, and Ile-256 while the phenolic hydroxy group forms hydrogen bonds with the thiol of Cys-283 and a water molecule, as well as an intramolecular hydrogen bond with the amide of the ligand itself.

The hydrophilic portion of the ligand mimics 2-OG interactions with the protein. Other positionings of 2-OG within the core of the enzyme may not be postulated, as only a narrow trough is available for binding and that only one buried positive charge (Arg-383) presents itself for pairing with the 2-OG ω-carboxylic acid. Positioning of 2-OG relative to the rest of the binding site is dependent on the location of the positively charged counter-ion (Arg-383) buried inside the beta-basket. Since in other oxygenases the direction of the 2-OG relative to the metal-binding site may differ by as much as 90 degrees, knowledge of 2-OG position may be important. Comparison of aligned structures shows, for example, that CAS has Arg-293 positioned in a similar way to Arg-383 in EGLN1 suggesting that 2-OG is oriented similarly in both enzymes. Further underscoring this analogy, the buried Arg-293 in the CAS structure is neutralized by a bound acetate ion positioned almost exactly in the same way as the ω-carboxylic acid of 2-OG in EGLN1-CD. In contrast, the structure of FIH shows that the 2-OG is rotated ~60° relative to EGLN1.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for identifying candidate compounds that bind to Hypoxia Inducible Factor-1 alpha prolyl hydroxylase (EGLN1), comprising the steps of:
   a) generating a three-dimensional model of an EGLN1 polypeptide, wherein the three-dimensional model has the atomic coordinates as shown in Table 2;
   b) identifying amino acid residues forming a catalytic domain of EGLN1 from the three-dimensional model of (a), wherein the catalytic domain comprises amino acid residues Ile-256, Tyr-283, Met-299, Gly-307, Tyr-310, His-313, Asp-315, Tyr-329, Leu-343, His-374, Val-376, Arg-383, and Trp-389, wherein the amino acid residues have the atomic coordinates in Table 2;
   c) generating a three-dimensional model of the catalytic domain of EGLN1;
   d) using the three-dimensional model of the catalytic domain of EGLN1 to design or select a candidate compound that binds to EGLN1; and
   e) evaluating the ability of the compound to bind EGLN1 in an in vitro, in vivo, or ex vivo assay.

2. A method according to claim 1, wherein step (d) comprises designing a candidate compound de novo.

3. A method according to claim 1, further comprising modifying the candidate compound based upon the positioning, alignment, and interactions between the candidate compound and one or more amino acids comprising the catalytic domain.

4. A method according to claim 1, wherein the results of the evaluation in step (e) provide further structure related binding information such that other candidate compounds are selected for evaluation in step (e).

5. A method according to claim 1, wherein the compound is evaluated in step (e) using an enzymatic assay.

6. A method according to claim 1, wherein the compound is evaluated in step (e) using a cell-based assay.

7. A method for identifying candidate compounds that bind to Hypoxia Inducible Factor-1 alpha prolyl hydroxylase (EGLN1), comprising the steps of:
   a) generating a three-dimensional model of an EGLN1 polypeptide, wherein the three-dimensional model has the atomic coordinates as shown in Table 2;

b) identifying amino acid residues forming a catalytic domain of EGLN1 from the three-dimensional model of (a), wherein the catalytic domain comprises amino acid residues Ile-256, Tyr-283, Met-299, Gly-307, Tyr-310, His-313, Asp-315, Tyr-329, Leu-343, His-374, Val-376, Arg-383, and Trp-389, wherein the amino acid residues have the atomic coordinates in Table 2;

c) generating a modified three-dimensional model of the catalytic domain of EGLN1 by varying the relative position of the atoms that comprise the catalytic domain in step (b) such that the root mean square deviation of the structural coordinates of the conserved residue backbone atoms of the modified three-dimensional model is less than 1.5 Å when superimposed on the structural coordinates of Table 2;

d) using the modified three-dimensional model of the catalytic domain of EGLN1 to design or select a candidate compound that binds to EGLN1; and e) evaluating the ability of the compound to bind EGLN1 in an in vitro, in vivo or ex vivo assay.

8. A method according to claim 7, wherein step (d) comprises modifying the structure of the candidate compound.

9. A method according to claim 7, wherein step (d) comprises designing a candidate compound de novo.

10. A method according to claim 1, wherein the candidate compound selected in step (d) is in a virtual compound library.

11. A method according to claim 1, wherein the candidate compound selected in step (d) is known to bind to EGLN1 in vitro.

12. A method according to claim 1, wherein the modified three-dimensional model of the catalytic domain of EGLN1 is generated using a computer program that varies the atomic coordinates of the catalytic domain of EGLN1.

13. A method according to claim 7, wherein the candidate compound selected in step (d) is in a virtual compound library.

14. A method according to claim 1, wherein the method further comprises computationally evaluating fragments of a candidate compound in a series of steps wherein the best binding fragments are combined and are used to design a compound de novo.

15. A method according to claim 7, wherein the candidate compound selected in step (d) is known to bind to EGLN1 in vitro.

* * * * *

SEQUENCE LISTING

```
<160> NUMBER OF SEQ ID NOS: 15

<210> SEQ ID NO 1
<211> LENGTH: 255
<212> TYPE: PRT
<213> ORGANISM: Artificial
<220> FEATURE:
<223> OTHER INFORMATION: primer sequence

<400> SEQUENCE: 1

Glu Thr Val Arg Phe Gln Ser Leu Arg Pro Asn Gly Gln Thr Lys Pro
1               5                   10                  15

Leu Pro Ala Leu Lys Leu Ala Leu Glu Tyr Ile Val Pro Cys Met Asn
            20                  25                  30

Lys His Gly Ile Cys Val Val Asp Asp Phe Leu Gly Lys Glu Thr Gly
        35                  40                  45
```

```
Gln Gln Ile Gly Asp Glu Val Arg Ala Leu His Asp Thr Gly Lys Phe
    50                  55                  60
Thr Asp Gly Gln Leu Val Ser Gln Lys Ser Asp Ser Ser Lys Asp Ile
 65                  70                  75                  80
Arg Gly Asp Lys Ile Thr Trp Ile Glu Gly Lys Glu Pro Gly Cys Glu
                 85                  90                  95
Thr Ile Gly Leu Leu Met Ser Ser Met Asp Asp Leu Ile Arg His Cys
            100                 105                 110
Asn Gly Lys Leu Gly Ser Tyr Lys Ile Asn Gly Arg Thr Lys Ala Met
            115                 120                 125
Val Ala Cys Tyr Pro Gly Asn Gly Thr Gly Tyr Val Arg His Val Asp
130                 135                 140
Asn Pro Asn Gly Asp Gly Arg Cys Val Thr Cys Ile Tyr Tyr Leu Asn
145                 150                 155                 160
Lys Asp Trp Asp Ala Lys Val Ser Gly Gly Ile Leu Arg Ile Phe Pro
                165                 170                 175
Glu Gly Lys Ala Gln Phe Ala Asp Ile Glu Pro Lys Phe Asp Arg Leu
            180                 185                 190
Leu Phe Phe Trp Ser Asp Arg Asn Pro His Glu Val Gln Pro Ala
        195                 200                 205
Tyr Ala Thr Arg Tyr Ala Ile Thr Val Trp Tyr Phe Asp Ala Asp Glu
210                 215                 220
Arg Ala Arg Ala Lys Val Lys Tyr Leu Thr Gly Glu Lys Gly Val Arg
225                 230                 235                 240
Val Glu Leu Asn Lys Pro Ser Asp Ser Val Gly Lys Asp Val Phe
                245                 250                 255

<210> SEQ ID NO 2
<211> LENGTH: 277
<212> TYPE: PRT
<213> ORGANISM: Artificial
<220> FEATURE:
<223> OTHER INFORMATION: primer sequence

<400> SEQUENCE: 2

Met Ser Tyr Tyr His His His His His His Leu Glu Ser Thr Ser Leu
 1               5                  10                  15
Tyr Lys Lys Ala Gly Phe Glu Thr Val Arg Phe Gln Ser Leu Arg Pro
                20                  25                  30
Asn Gly Gln Thr Lys Pro Leu Pro Ala Leu Lys Leu Ala Leu Glu Tyr
             35                  40                  45
Ile Val Pro Cys Met Asn Lys His Gly Ile Cys Val Val Asp Asp Phe
 50                  55                  60
Leu Gly Lys Glu Thr Gly Gln Gln Ile Gly Asp Glu Val Arg Ala Leu
 65                  70                  75                  80
His Asp Thr Gly Lys Phe Thr Asp Gly Gln Leu Val Ser Gln Lys Ser
                 85                  90                  95
Asp Ser Ser Lys Asp Ile Arg Gly Asp Lys Ile Thr Trp Ile Glu Gly
            100                 105                 110
Lys Glu Pro Gly Cys Glu Thr Ile Gly Leu Leu Met Ser Ser Met Asp
        115                 120                 125
Asp Leu Ile Arg His Cys Asn Gly Lys Leu Gly Ser Tyr Lys Ile Asn
130                 135                 140
Gly Arg Thr Lys Ala Met Val Ala Cys Tyr Pro Gly Asn Gly Thr Gly
145                 150                 155                 160
```

```
Tyr Val Arg His Val Asp Asn Pro Asn Gly Asp Gly Arg Cys Val Thr
            165                 170                 175

Cys Ile Tyr Tyr Leu Asn Lys Asp Trp Asp Ala Lys Val Ser Gly Gly
            180                 185                 190

Ile Leu Arg Ile Phe Pro Glu Gly Lys Ala Gln Phe Ala Asp Ile Glu
            195                 200                 205

Pro Lys Phe Asp Arg Leu Leu Phe Phe Trp Ser Asp Arg Arg Asn Pro
            210                 215                 220

His Glu Val Gln Pro Ala Tyr Ala Thr Arg Tyr Ala Ile Thr Val Trp
225                 230                 235                 240

Tyr Phe Asp Ala Asp Glu Arg Ala Arg Ala Lys Val Lys Tyr Leu Thr
            245                 250                 255

Gly Glu Lys Gly Val Arg Val Glu Leu Asn Lys Pro Ser Asp Ser Val
            260                 265                 270

Gly Lys Asp Val Phe
            275

<210> SEQ ID NO 3
<211> LENGTH: 258
<212> TYPE: PRT
<213> ORGANISM: Artificial
<220> FEATURE:
<223> OTHER INFORMATION: primer sequence

<400> SEQUENCE: 3

Met Ser Tyr Tyr His His His His His Leu Arg Pro Asn Gly Gln
1               5                   10                  15

Thr Lys Pro Leu Pro Ala Leu Lys Leu Ala Leu Glu Tyr Ile Val Pro
            20                  25                  30

Cys Met Asn Lys His Gly Ile Cys Val Val Asp Phe Leu Gly Lys
            35                  40                  45

Glu Thr Gly Gln Gln Ile Gly Asp Glu Val Arg Ala Leu His Asp Thr
    50                  55                  60

Gly Lys Phe Thr Asp Gly Gln Leu Val Ser Gln Lys Ser Asp Ser Ser
65                  70                  75                  80

Lys Asp Ile Arg Gly Asp Lys Ile Thr Trp Ile Glu Gly Lys Glu Pro
                85                  90                  95

Gly Cys Glu Thr Ile Gly Leu Leu Met Ser Ser Met Asp Leu Ile
            100                 105                 110

Arg His Cys Asn Gly Lys Leu Gly Ser Tyr Lys Ile Asn Gly Arg Thr
            115                 120                 125

Lys Ala Met Val Ala Cys Tyr Pro Gly Asn Gly Thr Gly Tyr Val Arg
            130                 135                 140

His Val Asp Asn Pro Asn Gly Asp Gly Arg Cys Val Thr Cys Ile Tyr
145                 150                 155                 160

Tyr Leu Asn Lys Asp Trp Asp Ala Lys Val Ser Gly Gly Ile Leu Arg
                165                 170                 175

Ile Phe Pro Glu Gly Lys Ala Gln Phe Ala Asp Ile Glu Pro Lys Phe
            180                 185                 190

Asp Arg Leu Leu Phe Phe Trp Ser Asp Arg Arg Asn Pro His Glu Val
            195                 200                 205

Gln Pro Ala Tyr Ala Thr Arg Tyr Ala Ile Thr Val Trp Tyr Phe Asp
            210                 215                 220

Ala Asp Glu Arg Ala Arg Ala Lys Val Lys Tyr Leu Thr Gly Glu Lys
225                 230                 235                 240

Gly Val Arg Val Glu Leu Asn Lys Pro Ser Asp Ser Val Gly Lys Asp
```

245     250     255

Val Phe

<210> SEQ ID NO 4
<211> LENGTH: 39
<212> TYPE: DNA
<213> ORGANISM: Artificial
<220> FEATURE:
<223> OTHER INFORMATION: Primer sequence

<400> SEQUENCE: 4
gaaaccgttc gtttccagtc cctgcggccc aacgggcag         39

<210> SEQ ID NO 5
<211> LENGTH: 36
<212> TYPE: DNA
<213> ORGANISM: Artificial
<220> FEATURE:
<223> OTHER INFORMATION: primer sequence

<400> SEQUENCE: 5
gaaagctggg ttctagaaga cgtctttacc gaccga            36

<210> SEQ ID NO 6
<211> LENGTH: 52
<212> TYPE: DNA
<213> ORGANISM: Artificial
<220> FEATURE:
<223> OTHER INFORMATION: primer sequence

<400> SEQUENCE: 6
ggggacaagt ttgtacaaaa aagcaggctt cgaaaccgtt cgtttccagt cc    52

<210> SEQ ID NO 7
<211> LENGTH: 39
<212> TYPE: DNA
<213> ORGANISM: Artificial
<220> FEATURE:
<223> OTHER INFORMATION: primer sequence

<400> SEQUENCE: 7
ggggaccact ttgtacaaga aagctgggtt ctagaagac         39

<210> SEQ ID NO 8
<211> LENGTH: 42
<212> TYPE: DNA
<213> ORGANISM: Artificial
<220> FEATURE:
<223> OTHER INFORMATION: primer sequence

<400> SEQUENCE: 8
atggcacatc accaccacca tcacctgcgg cccaacgggc ag     42

<210> SEQ ID NO 9
<211> LENGTH: 42
<212> TYPE: DNA
<213> ORGANISM: Artificial
<220> FEATURE:
<223> OTHER INFORMATION: Primer sequence

<400> SEQUENCE: 9
ctgcccgttg ggccgcaggt gatggtggtg gtgatgtgcc at     42

<210> SEQ ID NO 10
<211> LENGTH: 747
<212> TYPE: DNA

```
<213> ORGANISM: Homo sapiens
<220> FEATURE:
<221> NAME/KEY: CDS
<222> LOCATION: (1)..(747)

<400> SEQUENCE: 10 ctg cgg ccc aac ggg cag acg aag ccc ctg ccg gcg ctg aag ctg gcg      48
Leu Arg Pro Asn Gly Gln Thr Lys Pro Leu Pro Ala Leu Lys Leu Ala
 1               5                  10                  15 ctc gag tac atc gtg ccg tgc atg aac aag cac ggc atc tgt gtg gtg      96
Leu Glu Tyr Ile Val Pro Cys Met Asn Lys His Gly Ile Cys Val Val
             20                  25                  30 gac gac ttc ctc ggc aag gag acc gga cag cag atc ggc gac gag gtg     144
Asp Asp Phe Leu Gly Lys Glu Thr Gly Gln Gln Ile Gly Asp Glu Val
         35                  40                  45 cgc gcc ctg cac gac acc ggg aag ttc acg gac ggg cag ctg gtc agc     192
Arg Ala Leu His Asp Thr Gly Lys Phe Thr Asp Gly Gln Leu Val Ser
     50                  55                  60 cag aag agt gac tcg tcc aag gac atc cga ggc gat aag atc acc tgg     240
Gln Lys Ser Asp Ser Ser Lys Asp Ile Arg Gly Asp Lys Ile Thr Trp
 65                  70                  75                  80 atc gag ggc aag gag ccc ggc tgc gaa acc att ggg ctg ctc atg agc     288
Ile Glu Gly Lys Glu Pro Gly Cys Glu Thr Ile Gly Leu Leu Met Ser
                 85                  90                  95 agc atg gac gac ctg ata cgc cac tgt aac ggg aag ctg ggc agc tac     336
Ser Met Asp Asp Leu Ile Arg His Cys Asn Gly Lys Leu Gly Ser Tyr
            100                 105                 110 aaa atc aat ggc cgg acg aaa gcc atg gtt gct tgt tat ccg ggc aat     384
Lys Ile Asn Gly Arg Thr Lys Ala Met Val Ala Cys Tyr Pro Gly Asn
        115                 120                 125 gga acg ggt tat gta cgt cat gtt gat aat cca aat gga gat gga aga     432
Gly Thr Gly Tyr Val Arg His Val Asp Asn Pro Asn Gly Asp Gly Arg
    130                 135                 140 tgt gtg aca tgt ata tat tat ctt aat aaa gac tgg gat gcc aag gta     480
Cys Val Thr Cys Ile Tyr Tyr Leu Asn Lys Asp Trp Asp Ala Lys Val
145                 150                 155                 160 agt gga ggt ata ctt cga att ttt cca gaa ggc aaa gcc cag ttt gct     528
Ser Gly Gly Ile Leu Arg Ile Phe Pro Glu Gly Lys Ala Gln Phe Ala
                165                 170                 175 gac att gaa ccc aaa ttt gat aga ctg ctg ttt ttc tgg tct gac cgt     576
Asp Ile Glu Pro Lys Phe Asp Arg Leu Leu Phe Phe Trp Ser Asp Arg
            180                 185                 190 cgc aac cct cat gaa gta caa cca gca tat gct aca agg tac gca ata     624
Arg Asn Pro His Glu Val Gln Pro Ala Tyr Ala Thr Arg Tyr Ala Ile
        195                 200                 205 act gtt tgg tat ttt gat gca gat gag aga gca cga gct aaa gta aaa     672
Thr Val Trp Tyr Phe Asp Ala Asp Glu Arg Ala Arg Ala Lys Val Lys
    210                 215                 220 tat cta aca ggt gaa aaa ggt gtg agg gtt gaa ctc aat aaa cct tca     720
Tyr Leu Thr Gly Glu Lys Gly Val Arg Val Glu Leu Asn Lys Pro Ser
225                 230                 235                 240 gat tcg gtc ggt aaa gac gtc ttc tag                                  747
Asp Ser Val Gly Lys Asp Val Phe
                245

<210> SEQ ID NO 11
<211> LENGTH: 248
<212> TYPE: PRT
<213> ORGANISM: Homo sapiens

<400> SEQUENCE: 11

Leu Arg Pro Asn Gly Gln Thr Lys Pro Leu Pro Ala Leu Lys Leu Ala
```

```
            1               5                  10                 15
Leu Glu Tyr Ile Val Pro Cys Met Asn Lys His Gly Ile Cys Val Val
                20                  25                  30

Asp Asp Phe Leu Gly Lys Glu Thr Gly Gln Gln Ile Gly Asp Glu Val
                35                  40                  45

Arg Ala Leu His Asp Thr Gly Lys Phe Thr Asp Gly Gln Leu Val Ser
    50                  55                  60

Gln Lys Ser Asp Ser Ser Lys Asp Ile Arg Gly Asp Lys Ile Thr Trp
65                  70                  75                  80

Ile Glu Gly Lys Glu Pro Gly Cys Glu Thr Ile Gly Leu Leu Met Ser
                85                  90                  95

Ser Met Asp Asp Leu Ile Arg His Cys Asn Gly Lys Leu Gly Ser Tyr
                100                 105                 110

Lys Ile Asn Gly Arg Thr Lys Ala Met Val Ala Cys Tyr Pro Gly Asn
                115                 120                 125

Gly Thr Gly Tyr Val Arg His Val Asp Asn Pro Asn Gly Asp Gly Arg
                130                 135                 140

Cys Val Thr Cys Ile Tyr Tyr Leu Asn Lys Asp Trp Asp Ala Lys Val
145                 150                 155                 160

Ser Gly Gly Ile Leu Arg Ile Phe Pro Glu Gly Lys Ala Gln Phe Ala
                165                 170                 175

Asp Ile Glu Pro Lys Phe Asp Arg Leu Leu Phe Phe Trp Ser Asp Arg
                180                 185                 190

Arg Asn Pro His Glu Val Gln Pro Ala Tyr Ala Thr Arg Tyr Ala Ile
                195                 200                 205

Thr Val Trp Tyr Phe Asp Ala Asp Glu Arg Ala Arg Ala Lys Val Lys
            210                 215                 220

Tyr Leu Thr Gly Glu Lys Gly Val Arg Val Glu Leu Asn Lys Pro Ser
225                 230                 235                 240

Asp Ser Val Gly Lys Asp Val Phe
                245

<210> SEQ ID NO 12
<211> LENGTH: 426
<212> TYPE: PRT
<213> ORGANISM: Homo spaiens

<400> SEQUENCE: 12

Met Ala Asn Asp Ser Gly Gly Pro Gly Gly Pro Ser Pro Ser Glu Arg
1               5                  10                  15

Asp Arg Gln Tyr Cys Glu Leu Cys Gly Lys Met Glu Asn Leu Leu Arg
                20                  25                  30

Cys Ser Arg Cys Arg Ser Ser Phe Tyr Cys Cys Lys Glu His Gln Arg
                35                  40                  45

Gln Asp Trp Lys Lys His Lys Leu Val Cys Gln Gly Ser Glu Gly Ala
    50                  55                  60

Leu Gly His Gly Val Gly Pro His Gln His Ser Gly Pro Ala Pro Pro
65              70                  75                  80

Ala Ala Val Pro Pro Arg Ala Gly Ala Arg Glu Pro Arg Lys Ala
                85                  90                  95

Ala Ala Arg Arg Asp Asn Ala Ser Gly Asp Ala Lys Gly Lys Val
                100                 105                 110

Lys Ala Lys Pro Pro Ala Asp Pro Ala Ala Ala Ser Pro Cys Arg
                115                 120                 125

Ala Ala Ala Gly Gly Gln Gly Ser Ala Val Ala Ala Glu Ala Glu Pro
```

```
            130                 135                 140
Gly Lys Glu Glu Pro Pro Ala Arg Ser Ser Leu Phe Gln Glu Lys Ala
145                 150                 155                 160

Asn Leu Tyr Pro Pro Ser Asn Thr Pro Gly Asp Ala Leu Ser Pro Gly
                165                 170                 175

Gly Gly Leu Arg Pro Asn Gly Gln Thr Lys Pro Leu Pro Ala Leu Lys
            180                 185                 190

Leu Ala Leu Glu Tyr Ile Val Pro Cys Met Asn Lys His Gly Ile Cys
                195                 200                 205

Val Val Asp Asp Phe Leu Gly Lys Glu Thr Gly Gln Gln Ile Gly Asp
210                 215                 220

Glu Val Arg Ala Leu His Asp Thr Gly Lys Phe Thr Asp Gly Gln Leu
225                 230                 235                 240

Val Ser Gln Lys Ser Asp Ser Lys Asp Ile Arg Gly Asp Lys Ile
                245                 250                 255

Thr Trp Ile Glu Gly Lys Glu Pro Gly Cys Glu Thr Ile Gly Leu Leu
                260                 265                 270

Met Ser Ser Met Asp Asp Leu Ile Arg His Cys Asn Gly Lys Leu Gly
            275                 280                 285

Ser Tyr Lys Ile Asn Gly Arg Thr Lys Ala Met Val Ala Cys Tyr Pro
            290                 295                 300

Gly Asn Gly Thr Gly Tyr Val Arg His Val Asp Asn Pro Asn Gly Asp
305                 310                 315                 320

Gly Arg Cys Val Thr Cys Ile Tyr Tyr Leu Asn Lys Asp Trp Asp Ala
                325                 330                 335

Lys Val Ser Gly Gly Ile Leu Arg Ile Phe Pro Glu Gly Lys Ala Gln
                340                 345                 350

Phe Ala Asp Ile Glu Pro Lys Phe Asp Arg Leu Leu Phe Phe Trp Ser
            355                 360                 365

Asp Arg Arg Asn Pro His Glu Val Gln Pro Ala Tyr Ala Thr Arg Tyr
            370                 375                 380

Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
                405                 410                 415

Pro Ser Asp Ser Val Gly Lys Asp Val Phe
            420                 425

<210> SEQ ID NO 13
<211> LENGTH: 407
<212> TYPE: PRT
<213> ORGANISM: Homo sapiens

<400> SEQUENCE: 13

Met Asp Ser Pro Cys Gln Pro Gln Pro Leu Ser Gln Ala Leu Pro Gln
1               5                   10                  15

Leu Pro Gly Ser Ser Glu Pro Leu Glu Pro Glu Pro Gly Arg Ala
                20                  25                  30

Arg Met Gly Val Glu Ser Tyr Leu Pro Cys Pro Leu Leu Pro Ser Tyr
            35                  40                  45

His Cys Pro Gly Val Pro Ser Glu Ala Ser Ala Gly Ser Gly Thr Pro
        50                  55                  60

Arg Ala Thr Ala Thr Ser Thr Thr Ala Ser Pro Leu Arg Asp Gly Phe
65                  70                  75                  80

Gly Gly Gln Asp Gly Gly Glu Leu Arg Pro Leu Gln Ser Glu Gly Ala
```

```
                          85                  90                  95
Ala Ala Leu Val Thr Lys Gly Cys Gln Arg Leu Ala Gln Gly Ala
            100                 105                 110

Arg Pro Glu Ala Pro Lys Arg Lys Trp Ala Glu Asp Gly Gly Asp Ala
            115                 120                 125

Pro Ser Pro Ser Lys Arg Pro Trp Ala Arg Gln Glu Asn Gln Glu Ala
            130                 135                 140

Glu Arg Glu Gly Gly Met Ser Cys Ser Cys Ser Ser Gly Ser Gly Glu
145                 150                 155                 160

Ala Ser Ala Gly Leu Met Glu Glu Ala Leu Pro Ser Ala Pro Glu Arg
            165                 170                 175

Leu Ala Leu Asp Tyr Ile Val Pro Cys Met Arg Tyr Tyr Gly Ile Cys
            180                 185                 190

Val Lys Asp Ser Phe Leu Gly Ala Leu Gly Gly Arg Val Leu Ala
            195                 200                 205

Glu Val Glu Ala Leu Lys Arg Gly Gly Arg Leu Arg Asp Gly Gln Leu
            210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
            245                 250                 255

Met Ala His Val Asp Ala Val Ile Arg His Cys Ala Gly Arg Leu Gly
            260                 265                 270

Ser Tyr Val Ile Asn Gly Arg Thr Lys Ala Met Val Ala Cys Tyr Pro
            275                 280                 285

Gly Asn Gly Leu Gly Tyr Val Arg His Val Asp Asn Pro His Gly Asp
            290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
            325                 330                 335

Val Ala Asn Ile Glu Pro Leu Phe Asp Arg Leu Leu Ile Phe Trp Ser
            340                 345                 350

Asp Arg Arg Asn Pro His Glu Val Lys Pro Ala Tyr Ala Thr Arg Tyr
            355                 360                 365

Ala Ile Thr Val Trp Tyr Phe Asp Ala Lys Glu Arg Ala Ala Ala Lys
            370                 375                 380

Asp Lys Tyr Gln Leu Ala Ser Gly Gln Lys Gly Val Gln Val Pro Val
385                 390                 395                 400

Ser Gln Pro Pro Thr Pro Thr
                405

<210> SEQ ID NO 14
<211> LENGTH: 239
<212> TYPE: PRT
<213> ORGANISM: Homo sapiens

<400> SEQUENCE: 14

Met Pro Leu Gly His Ile Met Arg Leu Asp Leu Glu Lys Ile Ala Leu
1               5                   10                  15

Glu Tyr Ile Val Pro Cys Leu His Glu Val Gly Phe Cys Tyr Leu Asp
                20                  25                  30

Asn Phe Leu Gly Glu Val Val Gly Asp Cys Val Leu Glu Arg Val Lys
            35                  40                  45

Gln Leu His Cys Thr Gly Ala Leu Arg Asp Gly Gln Leu Ala Gly Pro
```

```
                50                  55                  60
Arg Ala Gly Val Ser Lys Arg His Leu Arg Gly Asp Gln Ile Thr Trp
65                  70                  75                  80

Ile Gly Gly Asn Glu Glu Gly Cys Glu Ala Ile Ser Phe Leu Leu Ser
                85                  90                  95

Leu Ile Asp Arg Leu Val Leu Tyr Cys Gly Ser Arg Leu Gly Lys Tyr
                100                 105                 110

Tyr Val Lys Glu Arg Ser Lys Ala Met Val Ala Cys Tyr Pro Gly Asn
                115                 120                 125

Gly Thr Gly Tyr Val Arg His Val Asp Asn Pro Asn Gly Asp Gly Arg
                130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
                180                 185                 190

Arg Asn Pro His Glu Val Gln Pro Ser Tyr Ala Thr Arg Tyr Ala Met
                195                 200                 205

Thr Val Trp Tyr Phe Asp Ala Glu Glu Arg Ala Glu Ala Lys Lys Lys
    210                 215                 220

Phe Arg Asn Leu Thr Arg Lys Thr Glu Ser Ala Leu Thr Glu Asp
225                 230                 235

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: VARIANT
<222> LOCATION: 2-3
<223> OTHER INFORMATION: Xaa = any amino acid

<400> SEQUENCE: 15

Leu Xaa Xaa Leu Ala Pro Ala Ala
```